United States Patent [19]

Allen

[11] Patent Number: 4,481,243
[45] Date of Patent: Nov. 6, 1984

[54] PATTERN TREATED TISSUE PAPER PRODUCT

[75] Inventor: Patrick J. Allen, Cincinnati, Ohio

[73] Assignee: The Procter & Gamble Company, Cincinnati, Ohio

[21] Appl. No.: 568,476

[22] Filed: Jan. 5, 1984

[51] Int. Cl.³ .............................................. B32B 3/00
[52] U.S. Cl. .................................. 428/154; 428/156; 428/172; 428/165; 428/192; 428/194; 428/195; 428/211; 428/212; 428/297; 428/535
[58] Field of Search .............. 428/154, 156, 165, 170, 428/171, 172, 195, 211, 535, 192, 194, 212, 297

[56] References Cited

U.S. PATENT DOCUMENTS

| | | | |
|---|---|---|---|
| 3,293,683 | 12/1966 | Wyant | 428/535 |
| 3,377,224 | 4/1968 | Gresham et al. | 428/172 |
| 3,477,084 | 11/1969 | Thomas | 428/154 |
| 3,814,096 | 6/1974 | Weiss et al. | 128/296 |
| 3,896,807 | 7/1975 | Buchalter | 128/261 |
| 4,000,343 | 12/1976 | Pihl | 428/154 |
| 4,112,167 | 9/1978 | Dake et al. | 428/154 |
| 4,254,187 | 3/1981 | Claybaker | 428/535 |
| 4,277,529 | 7/1981 | Friedman | 428/211 |

Primary Examiner—James J. Bell
Attorney, Agent, or Firm—Monte D. Witte; Fredrick H. Braun; Richard C. Witte

[57] ABSTRACT

Strong, soft, absorbent tissue paper products comprising a substrate carrying an emollient. The substrate is planar and is a laminate formed of two or more tissue paper sheets. At least one of its two major surfaces must be soft, relatively untextured, and smooth. The emollient is distributed over at least a major portion of the smooth surface. In preferred embodiments, each tissue paper ply consists of two layers: the first is relatively weak compared to the second and has an outwardly facing surface which is soft, relatively untextured and smooth; the second layer is strong enough to impart to the ply sufficient strength to enable it to accomplish its intended purpose. The plies of tissue paper are joined together by a laminating means consisting of embossments in a region of embossing; the region of embossing is substantially free of emollient.

5 Claims, 3 Drawing Figures

PATTERN TREATED TISSUE PAPER PRODUCT

BACKGROUND OF THE INVENTION

1. Field of the Invention

This invention relates to strong, soft, absorbent tissue products such as facial tissues.

2. Background Art

The common cold and allergies with their associated weeping eyes and runny noses are a bane to mankind. In addition to the difficulties in breathing, seeing, talking, and disposing of nasal discharge, an individual afflicted with these disorders frequently must contend with a nose and areas surrounding it which are sore and irritated and which are, frequently, red and inflammed thereby calling the attention of others to his plight.

The irritation and infammation—the redness—can have several causes. A prime one is, of course, the sheer necessity of frequently blowing the nose into a tissue or cloth and wiping nasal discharge from the nose and the area surrounding it. The degree of irritation and inflammation caused by blowing and wiping is directly proportional to the surface roughness of the implement used. The degree of irritation and inflammation is also directly proportional to the number of times the nose and its surrounding areas must be contacted with an implement; the use of an implement which is relatively weak or relatively nonabsorbent will require a greater number of contacts with the face than will the use of a stronger or more absorbent implement which is able to contain a greater quantity of nasal discharge.

There have been numerous previous attempts to correct the problem of irritation and inflammation caused by blowing and wiping. One common approach has been to provide an implement which is smoother, softer, or both smoother and softer than previous implements. In modern industrialized societies, that implement is frequently a tissue paper product usually referred to as a facial tissue. Examples of such tissue paper products are shown in U.S. Pat. No. 4,300,981, which was issued to Carstens on Nov. 17, 1981 and in the various patents discussed in its specification. Other workers have applied emollients, salves, cleansing agents, and the like to substrates such as tissue paper in an attempt not only to enhance the cleaning of the skin but also to reduce irritation and inflammation either through the lubricity of the substance applied to the implement or through the therapeutic action of the substance. This approach has been applied by, for example, Dake et al. in U.S. Pat. No. 4,112,167 issued Sept. 5, 1978 particularly in regard to toilet tissues. It has also been followed by Buchalter in U.S. Pat. No. 3,896,807 issued July 29, 1975 and by Weiss et al. in U.S. Pat. No. 3,814,096 issued June 4, 1974.

Despite the efforts of numerous researchers, the problem of the red, sore nose of the cold or allergy sufferer has not yet been completely resolved.

Accordingly, it is an object of the present invention to provide a laminated tissue paper product which causes less irritation and inflammation to the nose and the facial areas surrounding it than do previously available products. It is a further object of this invention to provide a laminated tissue paper product which will serve as a source of emollient, salve, cleansing agent, or the like for application to the skin.

SUMMARY OF THE INVENTION

The present invention is a personal care product comprising a tissue paper substrate and an emollient carried by the substrate. The substrate is a planar material having two major surfaces at least one of which is soft, relatively untextured, and smooth. The emollient is distributed over at least a major portion of the smooth surface.

More particularly, the substrate comprises a laminate of at least two plies of tissue paper. At least one of the two plies is a layered tissue comprising a first layer and a second layer. The first layer is relatively weak compared to the second layer and has an outwardly facing surface which is soft, relatively untextured, and smooth; the second layer is strong enough to impart to the ply sufficient strength to enable it to accomplish its intended purpose, e.g., to provide a tissue strong enough and absorbent enough to contain nasal discharge during the nose blowing operation. The plies of the laminate are united only by patterns of embossments extending along the longitudinal edges of the product. The emollient is distributed over a major portion of at least one surface of the laminate, but the region containing the embossments is left substantially free of the emollient.

DETAILED DESCRIPTION OF THE INVENTION

Figure 1:
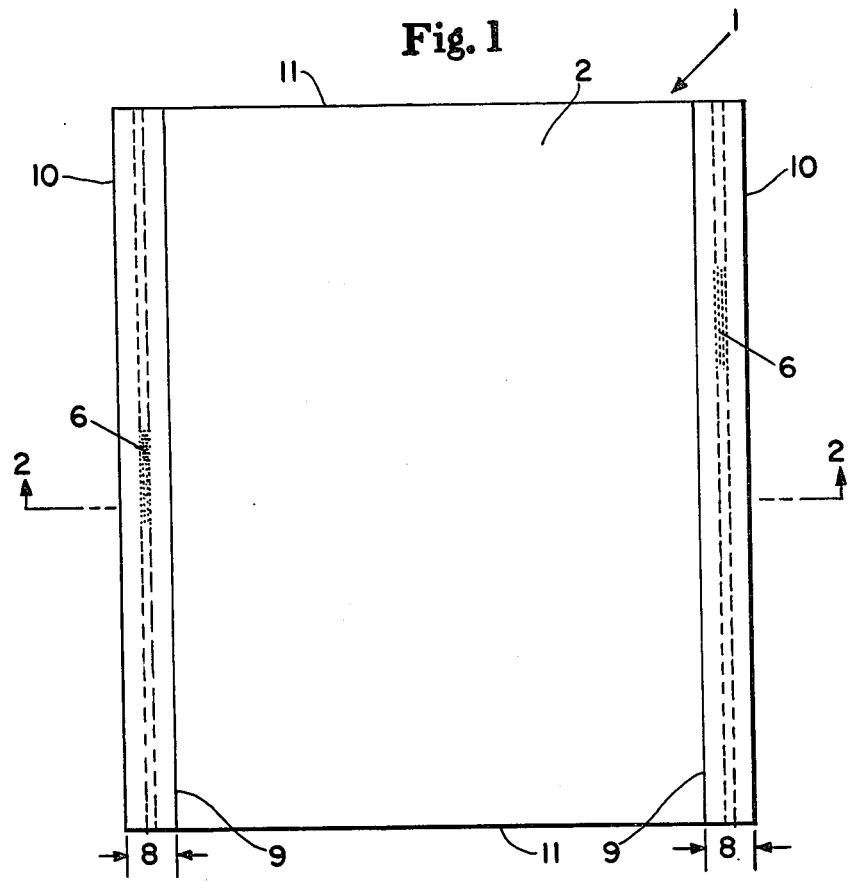
FIG. 1 is a plan view of the personal care product of this invention.

This invention is of a personal care product. More specifically it is of a tissue paper product which can be used to receive and contain discharges from the human body, which can be used to wipe portions of the human body to remove substances therefrom, and which can be used to deposit materials thereon. While the invention can take a number of forms, it will be discussed in terms of a common facial tissue.

The personal care product of this invention comprises two key elements: a substrate and an emollient which is carried by the substrate. Each element shall be discussed in turn.

The substrate is formed of a planar material commonly known as tissue paper. The substrate comprises a laminate of two or more plies of tissue paper. Since the substrate is formed of tissue paper, it is contemplated that it will be relatively thin in comparison to its dimensions in its major plane. As a relatively thin planar material, the substrate will have two major surfaces. At least one of the major surfaces must be soft and smooth.

"Soft" and "smooth" are, of course, relative terms. Softness is primarily a tactile sensation the user of a tissue paper product perceives as he holds the product, crumples it in his hand, and applies it to and passes it across various portions of his anatomy. Smoothness is also a tactile sensation which, while not unrelated to softness, can be considered to be a different attribute. A smooth article can be described as one which offers little resistance to passage across the skin. It can also be described as one having a relative absence of surface texture. The aforementioned U.S. Pat. No. 4,300,981, beginning in column 1, contains a more detailed description of softness and smoothness; this patent, in its entirety, is incorporated herein by reference.

In addition to softness and smoothness, the substrate must possess sufficient strength to allow it to accomplish its intended task. That is to say, it must have sufficient tensile strength, in both the wet and dry states, to maintain its physical integrity during nose blowing and wiping. The substrate must have a total tensile strength of at least about 235 grams per centimeter in the dry state. ("Total tensile strength" is the sum of the tensile strengths of the substrate as measured in the machine direction, MD, and in the cross machine direction, CD, by standard techniques.) It will also have a minimum CD tensile in the wet state of at least about 20 grams per centimeter. Preferably, the substrate will have a dry total tensile strength of at least about 315 grams per centimeter and a wet CD tensile strength of at least about 40 grams per centimeter. Further, the substrate should have a wet burst strength of at least about 60 grams. It has been discovered that a substrate which possesses these minimum strengths will withstand typical nose blowing and reduce the number of times the substrate must be placed in contact with the nose.

In addition to softness, smoothness, and strength, the substrate must be absorbent. It has been found that a substrate which will absorb at least about five grams of water per gram of substrate will possess adequate absorbency and will reduce the number of times the substrate must be passed across the nose to absorb nasal discharge.

In general, any planar, tissue paper material meeting the requirements of softness, smoothness, strength, and absorbency can be used in the substrate of the personal care product of this invention. The substrate will comprise a laminate formed of at least two plies of tissue paper.

Preferably, the tissue paper sheet in the laminate will be layered tissue paper sheets.

Preferably, the tissue paper sheet in the laminate will be layered tissue paper sheets.

Strength in tissue paper is frequently achieved at the cost of softness, and vice versa. The use of layering in making tissue paper sheets tends to offset or counteract the usual relationships. Thus, a layered tissue paper sheet possesses at least one soft layer and at least one strong layer. It will then present to the user the soft, smooth, outwardly facing surface provided by the soft layer and will maintain its integrity during use because of the strength of the strong layer. Preferably, the layered tissue paper sheet used in the practice of this invention is a tissue paper sheet described with particularity in the hereinbefore incorporated U.S. Pat. No. 4,300,981.

More specifically, in the words of U.S. Pat. No. 4,300,981, the preferred layered tissue paper sheet has a substantially flat velutinous top surface and comprises a first layer comprising papermaking fibers and a second layer comprising substrate means for supporting the first layer and for providing the tissue paper sheet with sufficient tissue strength for its intended purpose. The first layer comprises a primary filamentary constituent of about 60% or more by weight of relatively short papermaking fibers having average lengths of from about 0.25 millimeter to about 1.50 millimeters. The velutinous top surface is the outwardly facing surface of the first layer; the surface is defined by the substantially unbonded free end portions of a multiplicity of the short papermaking fibers. The tissue paper sheet has an average top surface human-tactile-response texture (HTR-Texture) of about 1.5 or less, preferably 1.0 or less and the velutinous top surface has an average free-fiber-end-index (FFE-Index) of at least about 60. The second layer normally comprises a primary fibrous material and is normally about 40% or more by weight of relatively long papermaking fibers having average lengths of at least about 2.0 millimeters. The tissue paper sheet preferably has a basis weight of from about 10 to about 65 grams per square meter and the first layer has a basis weight of from about 5 to about 57 grams per square meter. (The basis weights are measured while the sheet is in the uncreped state.)

In an alternate embodiment of the tissue paper sheet, still as described in U.S. Pat. No. 4,300,981, the layered tissue paper sheet comprises a third layer of papermaking fibers juxtaposed the opposite side of the second layer from the first layer. This second layer can comprise a principal filamentary constituent of about 60% or more by weight of relatively short papermaking fibers having average lengths of about 1.5 millimeters or less and can have a velutinous outwardly facing surface (opposite the surface provided by the first layer) which has an average HTR-Texture of about 1.5 or less, preferably 1.0 or less, and an average FFE-Index of about 60 or more. In point of fact, the third layer can be substantially identical to the first layer.

As noted, the substrate comprises a laminate of at least two plies of tissue paper. At least one major surface of the laminate must be soft and smooth and the laminate as a whole must be strong and absorbent. The plies comprising the laminate can be identical or they can be different.

While any tissue paper sheets can be used as the plies of the laminate, so long as the laminate possesses the requisite qualities, the laminate described in the hereinbefore incorporated U.S. Pat. No. 4,300,981 is preferred. In the words of that patent, the substrate is a two-ply sheet type tissue paper laminate having a substantially flat velutinous top surface. The laminate comprises a first ply of tissue paper and a second ply of tissue paper in juxtaposed relation. The first ply is a two-layer tissue paper sheet comprising a first layer and a second layer. The first layer comprises a primary filamentary constituent of about 60% or more by weight of relatively short papermaking fibers having average lengths of from about 0.25 millimeter to about 1.5 millimeters. The velutinous top surface is the outwardly facing surface of the first layer and is defined by substantially unbonded free end portions of a multiplicity of the short papermaking fibers. The sheet has an average HTR-Texture of about 1.5 or less and the velutinous surface has an average FFE-Index of at least about 60. In an alternate, and preferred, embodiment, the second layer comprises a substrate means for supporting the first layer and for providing the ply with sufficient tensile strength for its intended purpose. The second layer comprises about 40% or more by weight of relatively long papermaking fibers having average length of about 2.0 millimeters or more.

In another preferred laminate substrate, the laminate comprises a first ply of tissue paper as described above and a second ply of tissue paper comprising an upper layer of papermaking fibers and a lower layer comprising substrate means for supporting the upper layer and for providing the second ply with sufficient tensile strength for its intended purpose. The upper layer comprises a first filamentary constituent of about 60% or more by weight of relatively short papermaking fibers having average length of from about 0.25 millimeter to about 1.5 millimeters. The upper layer further has an outwardly facing velutinous surface defined by substantially unbonded free end portions of a multiplicity of the short fibers. The second ply has an average upper layer HTR-Texture of about 1.5 or less and the velutinous surface of the upper layer has an average FFE-Index of about 60 or more. The first and second plies are associated with the second layer of the first ply being juxtaposed the lower layer of the second ply whereby both outwardly facing surfaces of the laminate are velutinous surfaces. The two plies have basis weights within the ranges described above.

The description of the laminate substrate immediately above is of a laminate comprising two plies of tissue paper. While this is a preferred embodiment, it is not to be inferred that laminates comprising three or more plies are not suitable for use in the present invention.

In the laminate substrate, the various plies are held in juxtaposed relation by laminating means. This laminating means can be any embossing means known to those skilled in the art. Preferrably, the plies are laminated by embossing and without the use of adhesives. For example, U.S. Pat. No. 3,317,224 issued to Gresham et al. on Apr. 9, 1968 and incorporated herein by reference exhibits one method of fixing together plies of thin paper. Another suitable technique for combining two tissue paper sheets into a laminate is the apparatus shown in FIG. 20 of the hereinbefore incorporated U.S. Pat. No. 4,300,981.

Preferably, the tissue paper sheets are united one to another in juxtaposed relation by a pattern of embossments extending along the longitudinal edges of the laminate. When the laminate consists of two tissue paper sheets, the sheets are preferably free to move with respect to one another except in the region of the pattern of embossments. The preferred pattern of embossments is described with particularity hereinafter.

The second necessary element of the present invention is an emollient. As used in this specification, an emollient is a material which softens, soothes, supples, coats, lubricates, moisturizes, or cleanses the skin. In preferred embodiments, the emollient accomplishes several of these objectives such as soothing, moisturizing, and lubricating the skin. The emollient can take the form of a lotion, a cream, a gel, or a solid. Dake et al., Buchalter, and Weiss et al., in the aforementioned U.S. patents, all three of which are incorporated herein by reference, describe emollients which can be used in the practice of the present invention.

Especially preferred is an emollient comprising from about 51% to about 81% by weight mineral oil, from about 14% to about 34% cetearyl alcohol (a mixture of fatty alcohols consisting predominately of cetyl and steryl alcohols) and from about 5% to about 15% steareth-2 (polyethyleneglycol ethers of steryl alcohol which conform to the formula:

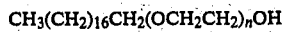

$$CH_3(CH_2)_{16}CH_2(OCH_2CH_2)_nOH$$

where n has an average value of 2).

The emollient can be applied to the substrate by any convenient technique such as spraying, dipping, padding, or, in the case of the preferred emollient and other substances having similar physical properties, by extrusion of the melted emollient onto the substrate.

The emollient is applied at least to the soft, smooth, major surface of the substrate. Preferably, and especially when both surfaces of the substrate are soft and smooth as used herein, the emollient is applied to both major surfaces of the substrate. It can be applied to the substrate at any convenient level. The preferred emollient is applied to the substrate at a level of from about 0.8 to about 8 grams per square meter to each side of the preferred laminate substrate.

Preferably, the emollient is essentially uniformly distributed over a major portion of at least one major surface of the substrate. While the emollient can be distributed over only a minor portion, or portions, of the substrate, such an arrangement is not preferred.

In choosing emollients, those skilled in the art can readily select compositions which do not deleteriously interact with the substrate, which are economical to use, which are safe for use on human skin, which can be conveniently applied to the substrate, and which are easily released from the substrate to the skin by the simple act of wiping the personal care product across the skin. Likewise, those skilled in the art can readily determine the quantity of emollient to be applied to any given area of substrate. Factors to be taken into consideration include the cost of the emollient, its physical characteristics, the quantity which should be applied to the skin to accomplish the goal of soothing, protecting, etc., providing an aesthetically pleasing physical appearance, and convenience of packaging.

As noted above, the emollient is preferably distributed over a major portion of both major surfaces of the substrate. In the personal care product of this invention having a laminate substrate, the emollient is distributed over a major portion of both major surfaces of the laminate, but a region extending along each longitudinal edge of the substrate is left substantially free of emollient. One version of this invention is shown in FIGS. 1, 2, and 3.

Figure 2:
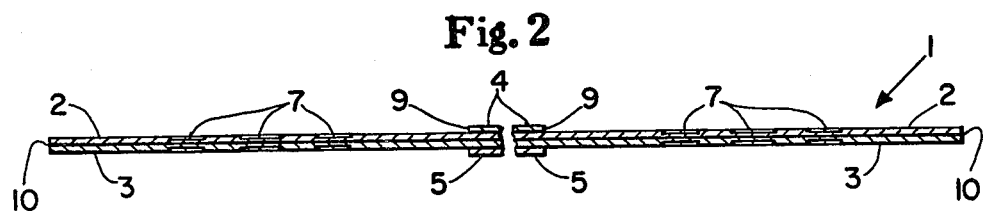
FIG. 2 is an enlarged cross sectional view of the personal care product shown in FIG. 1 taken along line 2—2; the thickness of certain elements has been greatly exaggerated for clarity.
Figure 3:
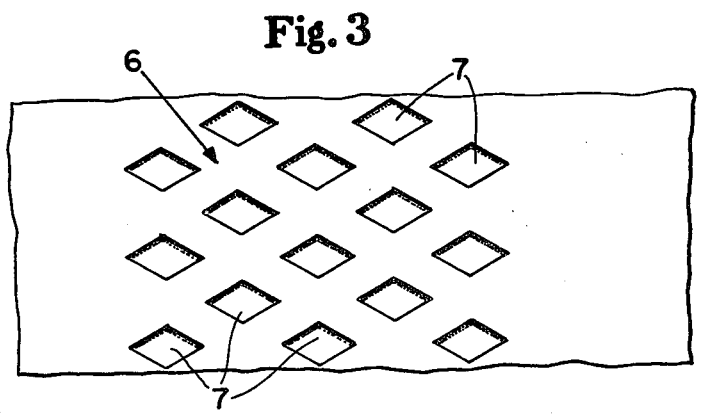
FIG. 3 is an enlarged view of a portion of the personal care product of FIG. 1 illustrating one arrangement of embossments which constitutes the pattern of embossments used in the union of the plies of the personal care product.

Facial tissue 1 is illustrated in plan view in FIG. 1 and in cross sectional view taken along line 2—2 in FIG. 2. In FIG. 2, facial tissue 1 is shown greatly enlarged for clarity; the thickness of certain elements has also been exaggerated for clarity.

Facial tissue 1 comprises first tissue 2 and second tissue 3. First and second tissues 2 and 3 are preferably identical and preferably comprise the layered tissue paper sheets discussed at length above. (Layers within first and second tissues 2 and 3 are not illustrated in FIG. 2.) Facial tissue 1 has longitudinal edges 10 and longitudinal edges 11. It is coated on both major surfaces with emollient 4 and 5. (While emollient 4 and 5 are shown as a surface coating in FIGS. 1 and 2, it is to be understood that the emollient will penetrate to a greater or lesser extent through the thickness of first and second tissues 2 and 3 depending upon the exact nature of the emollient and of the tissues.)

First and second tissues 2 and 3 are united by a pattern of embossments 6 extending through embossing regions 8 adjacent to and generally parallel to longitudinal edges 10. In the version of facial tissue 1 illustrated in FIGS. 1 and 2, emollient 4 and 5 is applied substantially uniformly over the major portion of the major surfaces of facial tissue 1 essentially continuously between longitudinal edges 11 and essentially continuously between limits of emollient 9. As can be observed from the figures, embossing region 8 is left substantially free of emollient.

In the embodiments illustrated in FIGS. 1 and 2, the embossing regions extend adjacent longitudinal edges 10. While this is a preferred configuration, it is to be understood that the embossing regions could extend in an analagous member along latitudinal edges 11. These regions could also extend along all four edges of the product; it is necessary only that they extend along at least one of the edges which is for convenience, denominated the longitudinal edge. It is conceivable, but not preferred, that the region of embossment which is left free of emollient could extend across the tissue in one or more zones spaced apart from any of the edges of the tissue. It is also conceivable, though not preferred, that facial tissue 1 could have a configuration other than rectangular; in this situation the embossing region which is free of emollient could take some geometric form other than a rectangle.

As illustrated, first and second tissues 2 and 3 are united by laminating means comprising a pattern of embossments 6. An enlarged view of this pattern of embossments, 6 is shown in FIG. 3. It can be observed from FIG. 3 that pattern of embossments 6 comprises a multiplicity of individual embossments 7.

In the embodiment illustrated in FIG. 3, pattern of embossments 6 comprises a multiplicity of diamond shaped individual embossments 7 in bilaterally staggered array in five generally parallel rows. In this preferred configuration, pattern of embossments 6 is from about 0.5 to about 0.75 centimeter wide and extends completely along each longitudinal edges 10 of facial tissue 1. The individual embossments 7 are diamond shapes having a major point to point dimension of from about 0.9 to about 1.1 millimeters and a minor point to point dimension of from about 0.4 to about 0.6 millimeter. The diamond shaped embossments 7 are spaced from about 0.4 to about 0.6 millimeter between minor points in each row.

Embossing region 8 is left substantially free of emollient because it has been surprisingly discovered that the presence of emollient in the region tends to weaken the union effect of pattern of embossments 6. This weakening of the union effect occurs when the emollient is applied to the laminate prior to the union of first and second tissues 2 and 3 by embossment. In fact, it is essentially impossible to unite first and second tissues 2 and 3 by embossment after either or both are coated with emollient if the embossing regions are not substantially free of emollient.

The personal care product of this invention, when in the embodiment of a facial tissue, can be presented to the user in a variety of ways. Preferably, it is in the form of a rectangular facial tissue which is folded into the common facial tissue "C-fold" configuration and stacked. A covenient number of C-folded tissues is then placed within a container such as a paper board carton commonly used for facial tissues. Preferably, the carton is provided with an interior barrier which is impermeable to the emollient used in this invention; this barrier prevents emollient from migrating from the products of this invention into and through the top, sides, and bottom of the carton thereby giving a soiled and untidy appearance to the carton. In an alternate configuration, the personal care product of this invention is presented in the form of a facial tissue in an interlocking Z-fold in a carton as well known to those skilled in the art. Alternatively, though not preferred, the personal care product of this invention can be in the form of a continuous length of product presented to users in the form of a roll of product with lines of perforations extending at intervals atitudinally across the product much as paper towels and toilet tissues are commonly presented to consumers.

In the preferred embodiment facial tissue, the product is from about 15 to about 25 centimeters wide and from about 20 to about 25 centimeters long. The tissues are either C-folded or Z-folded.

It is to be understood that the present invention can be applied to products other than facial tissue, such as toilet tissue and the like.

The following examples are presented by way of illustration and not by way of limitation.

EXAMPLE I

Tissue paper is prepared generally as described in Example 3 of U.S. Pat. No. 4,300,981. The furnish used to form the first layer comprises Eucalyptus Hardwood Kraft fibers, the second Northern Softwood Kraft (NSK) fibers. Kymene 557 H polyamide-epichlorohydrin wet strength resin (as made by Hercules, Incorporated of Wilmington, Del.) is added to the NSK furnish at a level of about 1% by weight of fiber. The overall content of the tissue paper as a whole is about 40% (by weight, bone dry fiber basis) Eucalyptus and 60% NSK. The basis weight of the tissue paper is about 17 grams per square meter. A laminate is formed from two sheets of the tissue paper by embossing as shown in FIG. 3 and as described above. The velutinous surface of each ply faces outwardly. An emollient comprising 66% (by weight) mineral oil, 24% cetearyl alcohol, and 10% steareth-2 is melted and extruded onto the laminate at a rate of about 3.2 grams per square meter of surface to essentially the total area of each side of the laminate. The coated laminate exhibits an HTR-Texture of about 0.3 and an FFE-index of about 125. When cut into individual sheets about 24.4 centimeters by about 20.8 centimeters, the coated laminate provides a facial tissue which causes less irritation and inflammation to the nose than do conventional facial tissues.

EXAMPLE II

Example I is repeated except that the emollient is applied to the velutinous surface of each tissue ply immediately prior to the union of the plies by embossing. The emollient is applied only to the central portion of the tissue and the embossing regions, each about 16 millimeters wide and extending adjacent the longitudinal edge of the laminate, as illustrated in FIGS. 1 and 2, are left substantially free of emollient. The plies are united significantly more strongly than when the emollient encroaches into the embossing regions as in Example I. The product of this Example II causes less irritation and inflammation to the nose than do conventional facial tissues.

What is claimed is:

1. A personal care product comprising a planar substrate and an emollient carried by said substrate; said substrate comprising a laminate; said laminate comprising at least two plies of tissue paper in juxtaposed relation; said emollient being distributed over at least a major portion of at least one exposed surface of said substrate; said plies being united to form said laminate by a pattern of embossments in an embossing region;

said embossing region being substantially free of emollient.

2. A personal care product comprising a planar substrate and an emollient carried by said substrate; said substrate comprising a laminate; said laminate comprising at least two plies of tissue paper in juxtaposed relation; at least one of said plies comprising a first layer and a second layer; said first layer being weak relative to said second layer and having its outwardly facing surface soft, relatively untextured, and smooth; said second layer being sufficiently strong to impart sufficient strength to said ply to enable it to perform its intended function; said plies being oriented in said laminate so that said outwardly facing surface of said first layer forms one exposed surface of said substrate; said emollient being distributed over at least a major portion of said exposed surface; said substrate comprising at least one longitudinal edge; said plies being united to form said laminate by a pattern of embossments in an embossing region; said embossing region extending generally parallel to and adjacent said longitudinal edge; said embossing region being substantially free of emollient.

3. The personal care product of claim 2 wherein at least two of said plies each comprise a first layer and a second layer; each of said first layers being weak relative to its associated second layer and having their outwardly facing surfaces soft, relatively untextured, and smooth; each of said second layers being sufficiently strong to impart sufficient strength to each of said plies to enable them to perform their intended functions; each of said plies being oriented in said laminate so that said outwardly facing surfaces of said first layers form the two exposed surfaces of said laminate with said second layers being disposed toward the interior of said laminate; and said emollient being distributed over at least a major portion of at least one of said exposed surfaces.

4. A personal care product comprising a planar substrate and an emollient carried by said substrate; said substrate being a two-ply sheet type tissue paper laminate having a substantially flat velutinous top surface; said laminate comprising a first ply of tissue paper and a second ply of tissue paper in juxtaposed relation; said first ply being a two-layer tissue paper sheet comprising a first layer and a second layer; said first layer comprising a primary filamentary constituent of about 60% or more by weight of relatively short papermaking fibers average lengths of from about 0.25 mm to about 1.5 mm; said velutinous top surface being the outwardly facing surface of said first layer, which surface is defined by substantially unbounded free end portions of a multiplicity of said short fibers; said sheet having an average HTR-Texture of about 1.5 or less; and said velutinous surface having an average FFE-Index of at least about sixty; said emollient being distributed over at least a major portion of said velutinous top surface.

5. The personal care product of claim 4 wherein said second ply comprises an upper layer of papermaking fibers and a lower layer comprising substrate means for supporting said first layer and for providing said second ply with sufficient tensile strength for its intended purpose; said upper layer comprising a first filamentary constituent of about 60% or more by weight of relatively short papermaking fibers having average length of from about 0.25 mm to about 1.5 mm; said upper layer further having an outwardly facing velutinous surface defined by substantially unbonded free end portions of a multiplicity of said short fibers; said second ply having an average upper layer HTR-Texture of about 1.5 or less; and said velutinous surface of said upper layer having an average FFE-Index of about sixty (60) or more; said first and second plies being associated with said second layer of said first ply being juxtaposed said lower layer of said second ply whereby both outwardly facing surfaces of said laminate are velutinous surfaces.

* * * * *

UNITED STATES PATENT AND TRADEMARK OFFICE
CERTIFICATE OF CORRECTION

PATENT NO. : 4,481,243
DATED : November 6, 1984
INVENTOR(S) : PATRICK JAY ALLEN

It is certified that error appears in the above-identified patent and that said Letters Patent are hereby corrected as shown below:

Column 5, line 30, "U.S. Pat. No. 3,317,224" should read
-- U.S. Pat. No. 3,377,224 --

Column 8, line 5, "atitudinally" should read
-- latitudinally --

Signed and Sealed this

Fourth Day of June 1985

[SEAL]

Attest:

DONALD J. QUIGG

Attesting Officer    Acting Commissioner of Patents and Trademarks